(12) United States Patent
Ward (10) Patent No.: US 10,548,689 B2
(45) Date of Patent: Feb. 4, 2020

(54) ADJUSTABLE SEGMENTAL DISTALIZATION APPLIANCE FOR ORTHODONTIC TREATMENTS

(71) Applicant: Robert Ward, Winnipeg (CA)

(72) Inventor: Robert Ward, Winnipeg (CA)

( * ) Notice: Subject to any disclaimer, the term of this patent is extended or adjusted under 35 U.S.C. 154(b) by 0 days.

(21) Appl. No.: 15/882,381

(22) Filed: Jan. 29, 2018

(65) Prior Publication Data

US 2018/0214249 A1 Aug. 2, 2018

Related U.S. Application Data

(60) Provisional application No. 62/452,010, filed on Jan. 30, 2017.

(51) Int. Cl.
*A61C 7/10* (2006.01)
*A61C 7/00* (2006.01)

(52) U.S. Cl.
CPC . *A61C 7/00* (2013.01); *A61C 7/10* (2013.01)

(58) Field of Classification Search
CPC .......................................................... A61C 7/10
See application file for complete search history.

(56) References Cited

U.S. PATENT DOCUMENTS

| | | | | |
|---|---|---|---|---|
| 934,958 A * | 9/1909 | Case | ......................... | A61C 7/10 433/7 |
| 4,200,979 A * | 5/1980 | Wallshein | ................ | A61C 7/10 433/7 |
| 5,885,290 A * | 3/1999 | Guerrero | .............. | A61B 17/663 433/7 |
| 6,062,854 A * | 5/2000 | Pozzi | ....................... | A61C 7/10 433/18 |
| 6,139,316 A * | 10/2000 | Sachdeva | ............. | A61B 17/663 433/7 |
| 6,592,366 B2 * | 7/2003 | Triaca | ................... | A61B 17/663 433/173 |
| 6,976,839 B2 * | 12/2005 | Lluch | ....................... | A61C 7/00 433/18 |
| 7,156,654 B2 * | 1/2007 | Inman | ...................... | A61C 7/00 433/21 |
| 7,871,267 B2 * | 1/2011 | Griffith | ..................... | A61C 7/12 433/10 |

(Continued)

*Primary Examiner* — Ralph A Lewis

(74) *Attorney, Agent, or Firm* — Kyle R Satterthwaite; Ryan W Dupuis; Ade & Company Inc.

(57) ABSTRACT

An adjustable segmental distalization appliance for orthodontic treatments features elongated first and second components that cooperatively define a central body of the appliance spanning longitudinally between an anterior end of the first component and a distal end of the second component. First and second terminal heads are respectively carried at the anterior and distal ends and adapted for attachment to first and second teeth of a dental arch. The first and second components are arranged for selective longitudinal displacement relative to one another to adjust an overall length of the central body to adapt to a patient-specific mesial-distal distance between the first and second teeth of the dental arch. In one embodiment, one component is a tubular female component carrying a ratchet pawl, and the other component is an insertable male component with cooperating ratchet teeth for incremental extension of the central body.

21 Claims, 4 Drawing Sheets

(56) References Cited

U.S. PATENT DOCUMENTS

2003/0050641 A1\* 3/2003 Mommaerts ......... A61B 17/663
606/71
2004/0013996 A1\* 1/2004 Sapian .................... A61C 7/10
433/18

\* cited by examiner

ADJUSTABLE SEGMENTAL DISTALIZATION APPLIANCE FOR ORTHODONTIC TREATMENTS

CROSS-REFERENCE TO RELATED APPLICATIONS

This application claims benefit under 35 U.S.C. 119(e) of U.S. Provisional Application No. 62/452,010, filed Jan. 30, 2017, the entirety of which is incorporated herein by reference.

FIELD OF THE INVENTION

The present invention relates generally to Orthodontics, and more specifically to the resolution of dental anteroposterior (A-P) discrepancies between the maxillary (upper) and mandibular (lower) arches.

BACKGROUND

Auxiliary elements for segmental distalization are known in the prior art, including those disclosed in U.S. Pat. Nos. 6,976,839, 7,238,022 and 7,618,257 and U.S. Patent Applications 2006018883 and 20060257812, each of which is incorporated herein by reference in its entirety.

The non-adjustable segmental distalization elements of the prior art have several design characteristics that are not ideal for a clinician:

1) As prior art designs are not adjustable, the clinician must stock multiple different sizes (1 mm incremental lengths) in inventory. There is also variation in the arch length for the patient's right vs. left side which again increases necessary inventory (as elements are right and left side specific).
2) Prior art designs present challenges in intra-oral placement of the element as both terminal ends must be bonded simultaneously (technique sensitive). This increases risk of bond failure, and reduces efficiency of element placement.
3) Prior art designs present challenges with flush attachment seating at the canine terminal. The "flush or exact fit" is challenging with the inability to adjust the canine terminal end for angulation variation of the canine. Also 1 mm increments (length options currently available for elements) are not ideal, and present challenges to achieve flush fit at the canine terminal.

SUMMARY OF THE INVENTION

In view of the foregoing disadvantages inherent in the known types of apparatuses in the prior art, the present invention discloses an improved design for the segmental distalization of the canine-to-molar posterior maxillary or mandibular sector for orthodontic treatments. The present invention affords significant advantages over the currently known elements for this purpose.

According to a first aspect of the invention, there is provided an adjustable segmental distalization appliance for orthodontic treatments, said appliance comprising:
an elongated first component;
an elongated second component connected or connectable to said first elongated component to form an extension thereof in a longitudinal direction, whereby the elongated components cooperatively define a central body of the appliance spanning longitudinally between an anterior end of the first component and a distal end of the second component;
a first terminal head carried at the anterior end of the first component, said first terminal head comprising a first base pad facing laterally outward from the elongated first component and adapted for attachment to a first tooth of a dental arch; and
a second terminal head carried at the distal end of the second component, said second terminal head comprising a second base pad facing laterally outward from the elongated second component in a same direction as the first base pad and adapted for attachment to a second tooth of said same dental arch;
wherein said first and second components are arranged for selective longitudinal displacement relative to one another to adjust an overall length of the central body to adapt to a patient-specific mesial-distal distance between said first and second teeth of said dental arch.

Preferably said first and second components are lockable to one another at any of a plurality of user-selectable lengths of said central body.

Preferably the first and second components are self-locking to one another at each of said user-selectable lengths.

Preferably the first and second components are adapted to have a greater locking strength against displacement in a collapsing direction reducing the overall length of the central body than in an extending direction increasing the overall length of the central body.

Preferably the first and second components are adapted for incremental displacement therebetween to enable user-selection from any of a fixed number of pre-determined selectable lengths of said central body.

Preferably the first and second components are adapted for said incremental displacement in a direction increasing the overall length of the central body.

Preferably the first and second components are adapted for incremental displacement in increments of less than 1-mm.

Preferably one of said first and second components is a female tubular component, and the other of said first and second components is a male insertion component with an insertion end received or receivable in the female tubular component.

Preferably there is a ratchet mechanism defined between said first and second components by which said incremental displacement is enabled.

Preferably said ratchet mechanism comprises a set of ratchet teeth defined on one of said first and second components and a ratchet pawl defined on the other of said first and second components.

Preferably said one of the first and second components with the ratchet teeth is the male insertion component, and said other of the first and second components with the ratchet pawl is the female tubular component with a hollow interior in which the insertion end of said one of the first and second components with the ratchet teeth is received or receivable.

Preferably said first and second components each have an arcuate curvature in the longitudinal direction, and the ratchet teeth and the ratchet pawl are defined concave sides of the arcuate curvatures of the components.

Preferably said ratchet mechanism further comprises an operating lever by which the ratchet pawl is movable into a release position allowing the ratchet teeth to slide freely past said ratchet pawl.

Preferably the female tubular component comprises an opening in a circumferential wall thereof by which the operating lever is accessible from outside the female tubular component.

Preferably at least one of the first and second terminal heads is connected to the respective one of the first and second components by a respective single axis rotational joint by which said one of the first and second terminal heads is rotatable relative to the respective one of the first and second components about a singular axis shared thereby at said joint.

In embodiment, there are two respective single-axis rotational joints by which the first and second terminal heads are rotatably connected to the first and second components, respectively, for rotation relative thereto about first and second axes.

In another embodiment, said at least one single-axis rotational joint consists of only said one single-axis rotational joint.

Preferably the at least one single-axis rotational joint comprises at least one threaded screw joint.

According to a second aspect of the invention, there is provided a method of using the forgoing distalization appliance, said method comprising performing said relative longitudinal displacement of the first and second components to adjust the overall length of the central body according to the patient-specific mesial-distal distance between said first and second teeth of said dental arch, and attaching the first and second terminal heads to said first and second teeth of said dental arch with the central body set according to said patient-specific distance.

Preferably the method comprises lengthening said central body incrementally.

Preferably the method comprises lengthening said central body incrementally via a ratcheting action between the first and second components.

Preferably the method comprises using a self-locking action between the first and second components to maintain a selected overall length of the central body.

The method may comprise releasing the self-locking action between said first and second components, and with said self-locking action released, shortening said central body.

Preferably the method comprises angularly adjusting one of the terminal heads by rotating same about a respective axis of a joint by which the terminal head is rotatable about only said respective axis.

According to a third aspect of the invention, there is provided a segmental distalization appliance for orthodontic treatments, said appliance comprising:
an elongated central body spanning in a longitudinal direction in which opposing first and second ends of the central body are spaced;
a first terminal head carried at the first end of the central body and adapted for attachment to a first tooth of a dental arch; and
a second terminal head carried at the second end of the central body and adapted for attachment to a second tooth of said same dental arch;
wherein at least one of the first and second terminal heads is connected to the central body by a by a respective single axis rotational joint by which said one of the first and second terminal heads is rotatable relative to the central body about only a singular axis shared thereby at said joint.

According to a fourth aspect of the invention, there is provided a method of using the distalization appliance from the third aspect of the invention, said method comprising angularly adjusting said one of the terminal heads to a selected orientation by rotating said one of the terminal heads about the singular axis of the single-axis rotational joint while said single-axis rotational joint constrains said one of the terminal heads against movement about other axes, and attaching said one of the terminal heads to a respective one of the first and second teeth of the dental arch in the selected orientation.

The present invention thus provides a new construction of an adjustable segmental distalization appliance for orthodontic treatments, whereby the same can be utilized for increasing the accuracy, efficiency, and customizability of the segmental distalization element placement procedure.

In preferred embodiments, the adjustable segmental distalization element includes an arcuate two-piece length adjustable central body equipped at one end with a head for adaptation to the canine (angulation adjustable) and at the other end with a head for adaptation to the molar (rotation adjustable for maxillary molars and angulation adjustable for the mandible).

In preferred embodiments, both terminals employ mesh pad bases which can be bonded/coupled to the tooth surfaces preferably by an adhesive or other means. The central body is adjustable to every physiologically conceivable mesial-distal length between canine and molar teeth.

In preferred embodiments, the adjustable arcuate central body and terminals are arch specific, and have characteristics that allow the element to adapt to the maxillary or mandibular arches.

The advantages of an adjustable segmental distalization element include the following:
The ability to extend the element will reduce the technique sensitivity of placement.
Small adjustable increments (0.5 mm-1 mm) improve the fit of the element
"One size fits all" element reduces chair time (saves the clinician operating expense)
The reduced inventory requirements are also desirable from practice management viewpoint.

BRIEF DESCRIPTION OF THE DRAWINGS

The accompanying drawings of preferred embodiments of the invention, given as non-limiting examples, will assist the understanding thereof.

DETAILED DESCRIPTION OF PREFERRED EMBODIMENTS

Figure 1:
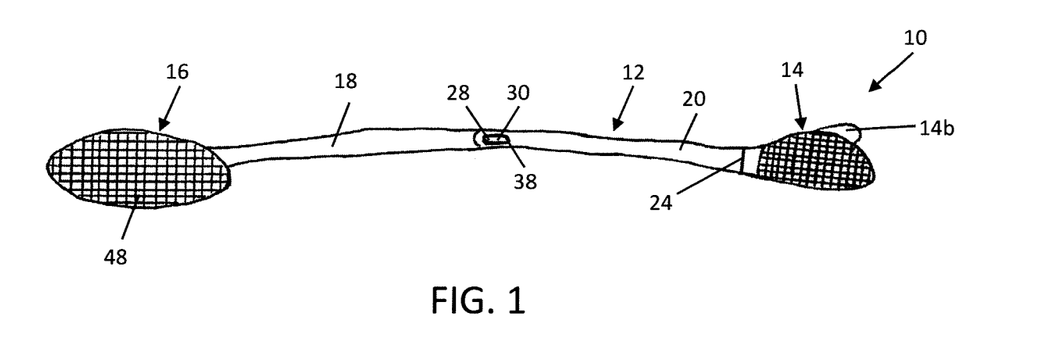
FIG. 1 is a lingual elevation view of a segmental distalization appliance for a maxillary dental arch.
Figure 2:
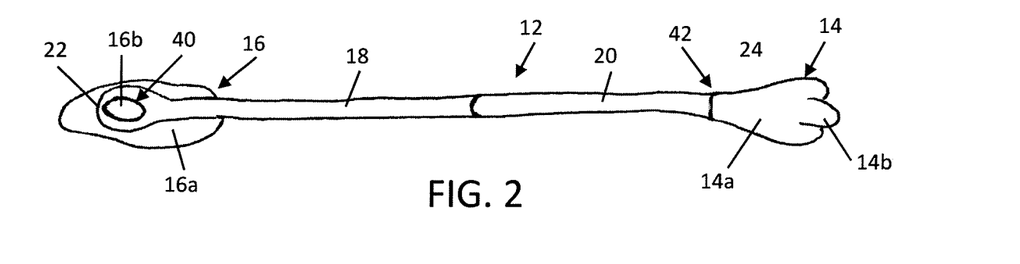
FIG. 2 is a buccal elevation view of the segmental distalization appliance of FIG. 1.
Figure 3:
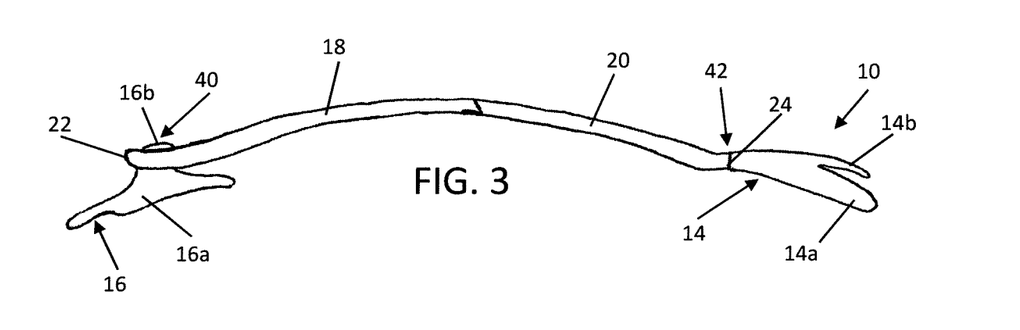
FIG. 3 is a superior plan view of the segmental distalization appliance of FIG. 1.
Figure 4:
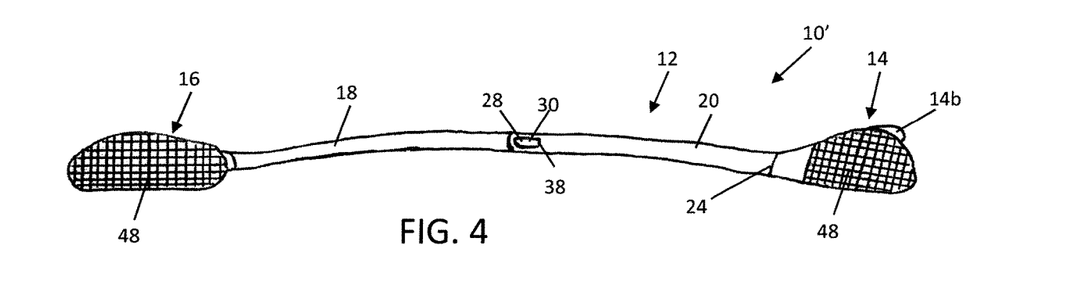
FIG. 4 is a lingual elevation view of a segmental distalization appliance for a mandibular dental arch.
Figure 5:
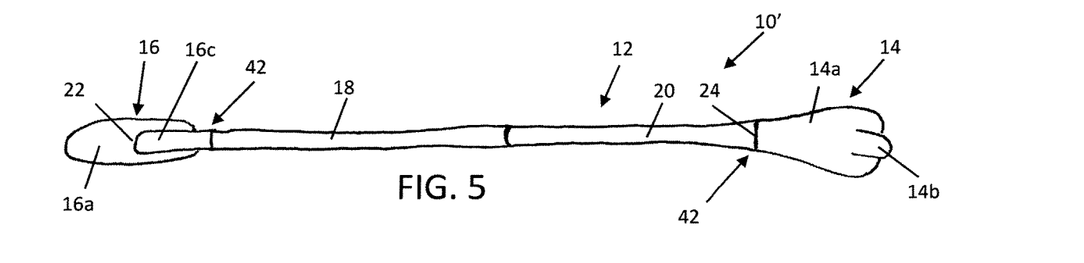
FIG. 5 is a buccal elevation view of the segmental distalization appliance of FIG. 4.
Figure 6:
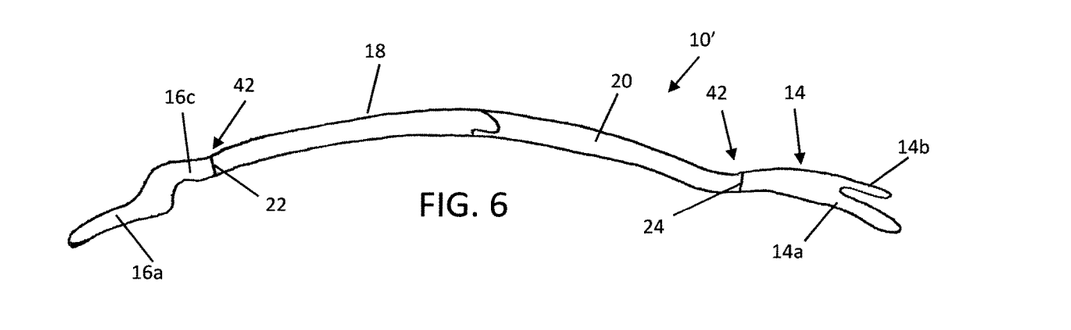
FIG. 6 is a superior plan view of the segmental distalization appliance of FIG. 4.

FIGS. 1 to 3 illustrate a first embodiment of a segmental distalization appliance 10 intended for use on a maxillary dental arch, while FIGS. 4 to 6 illustrate a similar second embodiment of the appliance 10' intended for use on a mandibular dental arch. The two embodiments differ from one another only in terms of the type of joint used between a central body 12 of the appliance and a distal terminal head 14 thereof intended for attachment to the patient's molar.

Otherwise, the two embodiments share the same structure for the central body 12, the distal terminal head 14 and an opposing anterior terminal head 16 intended for attachment to the patient's canine.

Description of Central Body

The central body 12 is comprised of male and female components 18, 20 assembled to form a unified rigid arm of arcuate curvature in a longitudinal direction separating an anterior end 22 of the body 12 from an opposing distal end 24 thereof. In the illustrated embodiments, the male component 18 defines the anterior end 22 of the central body and is comprised of a longitudinally arcuate arm with an integrated rack of ratchet teeth 26 on the concave side thereof, as illustrated in the cross-sectional views of FIGS. 7 and 8. In the present embodiment, the incremental distance from the point of one tooth to the next is less than 1 mm, preferably between 0.5 mm and 1.0 mm. Conversely, the female component 20 is comprised of a reciprocal, longitudinally arcuate tubular casing or housing with an integrated ratchet pawl 28 and release lever 30. In the illustrated embodiment, the rack of teeth 26 on the male component 18 span only a partial length thereof, starting from an insertion end 32 of the male component that opposes the anterior end 22 thereof in the longitudinal direction.

Figure 7:
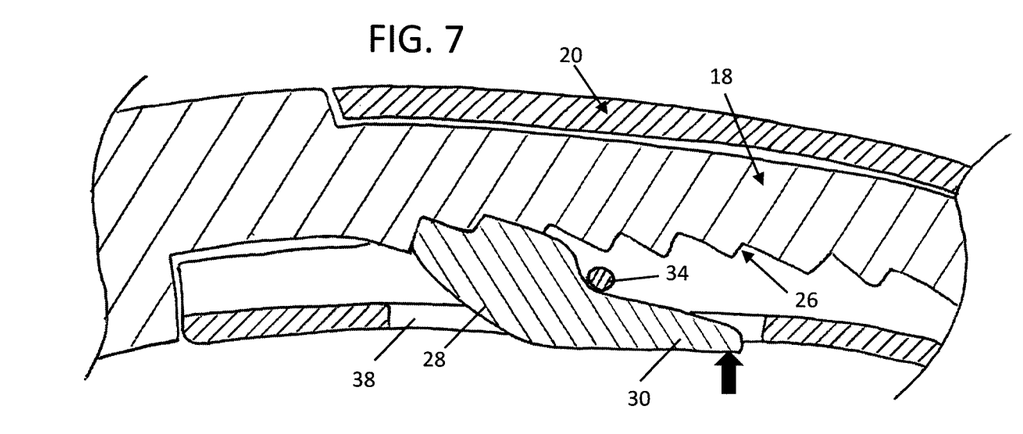
FIG. 7 is cross-sectional view of a central area of the distalization appliance of FIG. 2 or 5 as taken along line A-A thereof to illustrate a ratchet mechanism defined between mating male and female components of the appliance at said central area.

FIG. 7 illustrates the appliance in an assembled and fully-collapsed state in which an adjustable overall length of the central body 12, measured between the anterior and distal ends thereof, is at a minimum. In this state, the entire rack of teeth 26 are fully contained within the hollow interior of the female component. The ratchet pawl 28 is pivotally supported on the female component by a pivot pin 34 crossing transversely through the circumferential wall of the tubular female component in a direction perpendicular to the longitudinal direction and parallel to a reference axis from which the radial measure of the component's arcuate curvature is taken. The pivot pin 34 resides near an open end 36 of the female component that resides opposite the distal end 24 thereof. The pin 34 resides nearer to the concave side of the female component than to the opposing concave side thereof so as to leave most of the female component's hollow interior open, thereby providing sufficient space for the inserted male component to slide back and forth past the pin 34. An opening 38 in the circumferential wall of the female component at the concave side thereof accommodates the ratchet pawl 28 and release lever 30 therein, whereby the release lever 30 is accessible to the user from outside the female component. In the illustrated example, the release lever is an integral tab 30 extending from the pawl 28 to an opposing side of the pivot pin.

By means of a spring (not shown), the ratchet pawl 28 is normally biased into a default working position shown in FIG. 7, where a working end of the pawl engages with the rack of ratchet teeth 26 in a manner resisting, but not preventing, pulling of the male component 18 further outwardly through the open end 36 of the female component, while fully preventing pushing of the male component 18 further into the female component. Accordingly, in its default position, the ratchet pawl 28 allows pulling of the male component in a lengthening/extending direction drawing more of the male component out from the female component in order to lengthen the central body 12, but prevents pushing of the male member in the reverse collapsing/retracting direction reducing the overall length of the central body.

Figure 8:
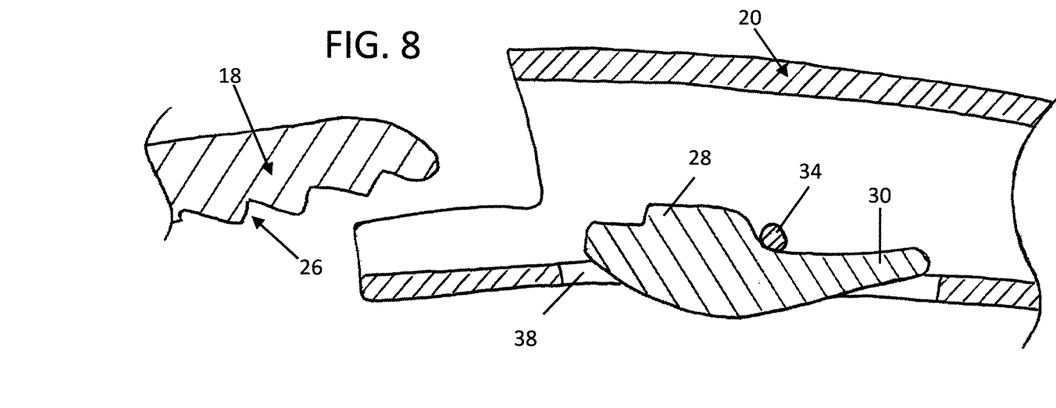
FIG. 8 is another cross-sectional view of the central area of the appliance in the same viewing plane as FIG. 7, but with the ratchet mechanism released and the male and female components uncoupled from one another.

In other words, the male and female components slide relatively past each other passively as the central arcuate body is extended in length, but the integrated ratchet action of the female component locks on the gear rack of the male component to prevent the components from sliding in the reverse collapsing/retracting direction. For the components to slide relative to one another in the reverse direction reducing the overall length of the unified central arcuate body 12, the clinician must depress the lever tab 30 on the female component inwardly toward the hollow interior thereof via the opening 38, thus pivoting the pawl 28 in the opposing direction out of engagement with the rack teeth 26 to release the male component into a freely slidable state in which it can be displaced longitudinally in either direction. When the pawl is engaged with the rack 26, it forces the outer surface of the convex side of the male member into abutment with the female component's concave inner surface situated across from the pawl-equipped side of the female component.

The pawl's engagement with the rack teeth thus defines a self-locking action between the male and female components, whereby these components are normally held together in fixed longitudinal relationship with one another, until either (a) the male member is pulled outwardly from the female member with sufficient force to allow the ratchet to slip incrementally from one tooth to the next, or (b) the release lever tab 30 is depressed to allow uninhibited free sliding of the male member in either direction. The central body 12 of the appliance will thus normally retain its given length until such action is taken to either lengthen or shorten the central body's overall length, as collectively defined by the longitudinally overlapping male and female components. The ratcheting action gives the user tactile and audible feedback on the incremental increase in length, whereby a user looking to increment the appliance's length by a particular multiple of the rack's tooth-to-tooth measurement simply counts the number of audible 'clicks' heard as the male component is pulled out from the female component, until the audible click count equals this desired multiple, thus confirming achievement of the desired lengthening of the central body 12.

Description of Joints

In the maxillary embodiment of FIGS. 1 to 3, the central arcuate body 12 connects to the distal terminal head 16 via a spherical bearing joint 40 at the distal end 22, and connects to the anterior terminal head 14 at the anterior end 24 via a threaded screw/bolt joint 42. In the mandibular embodiment of FIGS. 4 to 6, the central arcuate body 12 connects to the anterior and distal terminal heads by two respective threaded screw/bolt joints 42. In use of either appliance, the distal terminal head 16 is attached to the patient's molar on the given dental arch, and the anterior terminal head 14 is attached to the patient's canine on the same arch. Accordingly, the anterior terminal head 14 is referred to as such since it resides anteriorly of the distal terminal head 16 when the appliance is in place on the patient's dental arch.

The spherical bearing joint 40 in the maxillary embodiment is comprised of a spherically-contoured ball-like bearing protrusion 16b from the base pad 16 of the distal terminal head 16, and a spherically-contoured outer ring or socket integrally formed in the central arcuate body at the distal end 22 thereof. The spherical ball bearing and/or spherical ring may have built-in mechanical stops. These stops serve to purposefully limit the range of motion of the spherical bearing joint in certain planes of space. Use of such spherical joints in segmental distalizers is known from the aforementioned prior art, and thus not explicitly described herein.

Figure 9:
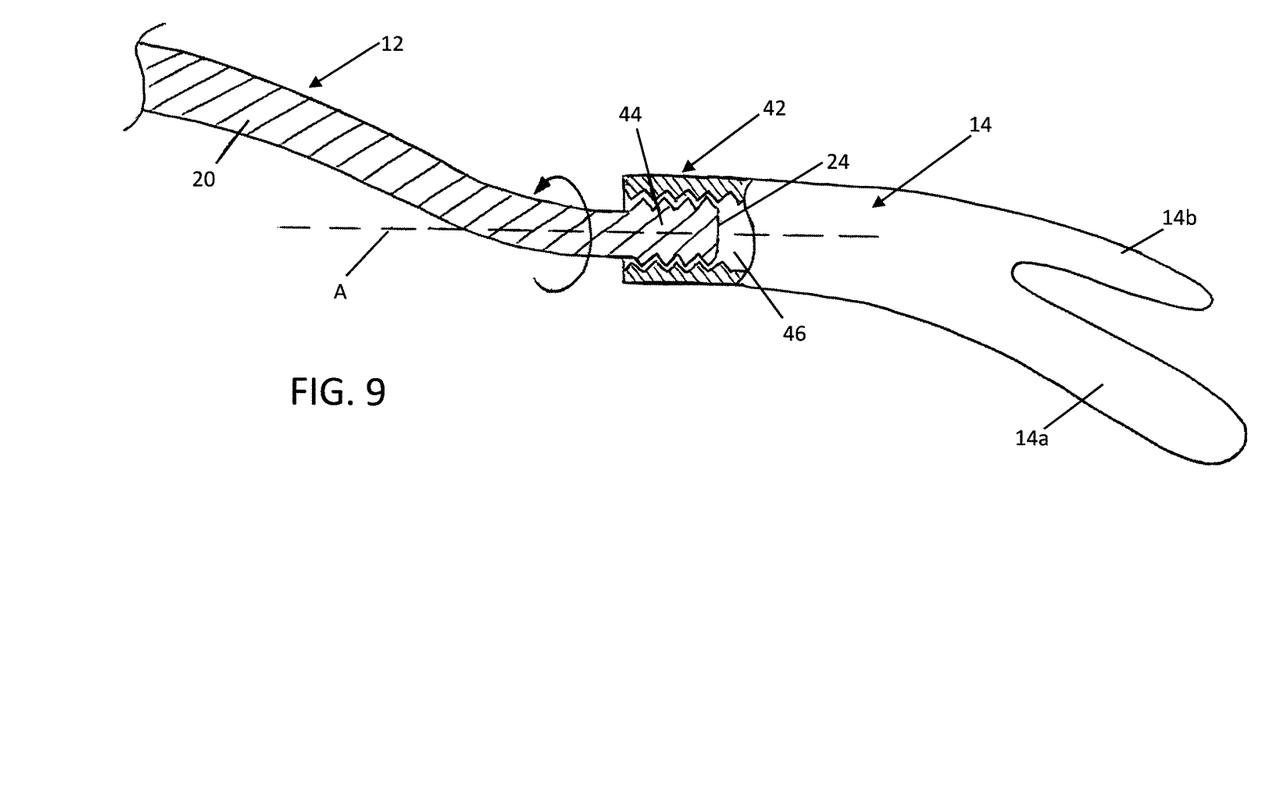
FIG. 9 is a cross-sectional view of an anterior end of the appliance of FIG. 2 or 5 as taken along line A-A thereof to illustrate a single-axis joint between an anterior terminal head and a central body of the appliance.

Turning to FIG. 9, each threaded screw/bolt joint 42 is comprised of external (male) helical threading 44 defined on the end of the respective component 20 of the central body 12, and a socket 46 with mating internal (female) helical threading at a coupling end of the respective terminal head 14. To enable operation of the mated threads, this threaded socket 46 is co-axial with the threaded end 24 of the respective body component 20 so that they share a common axis A about which the terminal head 14 can rotate relative to the body component 20.

The terminal head 14 is thus fastened to the central arcuate body 12 by the screw/bolt joint 42, but additionally, this variety of joint allows for variability in terminal rotation (adaptation to tooth angulation). That is, the threaded screw joint 42 enables the terminal head 14 to be rotated about the shared common axis A relative to the central body 12, thereby enabling adjustment of the orientation of the terminal head 14 to face an appropriate direction according to the angulation of the patient's tooth. The relative thread sizes between the body component and the terminal head are selected to provide a tight fit with a notable degree of rotational resistance, whereby the terminal head can be manually rotated with sufficient exertion, but requires some notable effort to do so in order to prevent inadvertent rotation once a desired angular orientation has been achieved.

This threaded screw joint 42 differs from the multi-directional spherical joint 40 used at the opposing end of the maxillary appliance in that it allows relative motion to occur between the central body and terminal head only about the singular shared axis A. Motion of the terminal head 14 about any other axis is constrained by the tightly mated threads. The threaded screw of the illustrated embodiment employs a singular thread count, the pitch and lead measurements of which are is selected to be relatively small, whereby a small degree of rotation of the terminal head about the axis A will cause only minimal axial displacement of the terminal so as to minimize the effect on the overall length of the appliance. The incremental ratcheting extension and collapse of the central body thus defines the primary length adjustment mechanism of the appliance.

Description of Terminals

The anterior terminal (canine terminal) consists of a base 14a, a hook 14b, and the internally threaded female socket 46 at the coupling end. The base has a mesh pad 48 undercoating that connects the terminal to the adhesive tooth bond interface. The hook 14b is a curved protrusion designed to temporarily retain orthodontic elastic bands during the distalization process. The internally threaded female socket 46 forms the threaded screw/bolt joint connection with the externally threaded anterior end 24 of the central arcuate body 12. Except for the internally threaded socket 46, the anterior end terminal 14 may be of similar structure to those of the prior art references cited herein, and therefore is not explicitly described herein in greater detail.

The distal terminal head (molar terminal) has two versions: one for the maxillary embodiment of FIGS. 1 to 3, and another for the mandibular embodiment of FIGS. 4 through 6.

The maxillary molar terminal in FIGS. 1 to 3 consists of a base 16a, and a spherical bearing protrusion 16b. The base has a mesh pad 48 undercoating that connects the terminal to the adhesive tooth bond interface. The spherical bearing protrusion 16b forms the spherical bearing joint with the spherical outer ring or socket of the respective component 18 of the central arcuate body.

The mandibular molar terminal in FIGS. 4 to 6 consists of a base 16a, and a bridge 16c with an internally threaded socket 46 matching that of FIG. 9. The base 16a once again has a mesh pad 48 undercoating that connects the terminal to the adhesive tooth bond interface. The base is connected to the central arcuate body 12 by a bridge 16c. The distal portion of the bridge connects to the base 16a at an acute angle. This angulation allows more efficient adaptation of the base mesh pad 48 to the molar. The proximal portion of the bridge houses an internally threaded socket 46 like that of FIG. 9. This internally threaded socket thus forms the screw/bolt joint 42 with the external helical thread at the respective end of the central arcuate body 12.

To use either appliance on the prescribed dental arch, the particular mesial-distal distance between the targeted molar and canine of the patient's arch is first gauged, and from its minimal-length fully-collapsed state, the central body of the appliance is extended incrementally by extension of the ratcheted male and female components until the overall effective length between the terminal heads of the appliances is set in accordance with the patient-specific mesial-distal measurement. If the male component is pulled to far out from the female component, overshooting the target length, the release lever tab 30 is depressed, and the central body collapsed back down past the target length by pushing the male component further back into the female component. The male component is then pulled out again in a step-wise manner, moving the rack tooth-by-tooth past the pawl by the appropriate number of increments to achieve the target length of the appliance. This selected length is then automatically held by the default spring biased position of the pawl against the rack while the clinician adheres the two terminal heads to the molar and canine of the patient's dental arch. Prior to this adhesion, the orientation of each terminal head can be adjusted as needed into a suitable orientation for best conformance with the patient's respective tooth.

While the illustrated embodiments have their distal (molar) terminal heads attached to the rack-toothed male component of the central body and their anterior (canine) terminal heads attached to the hollow tubular female component of the central body, this configuration may be reversed while still enabling the relative sliding displacement longitudinally between the two components to adjust the collective length of the central body. Also, while the illustrated embodiments employ threaded screw fittings to define the single-axis rotational joints, other joint types allowing rotational motion about a singular axis while preventing motion about other axes may alternatively be employed.

The invention claimed is:

1. An adjustable segmental distalization appliance for orthodontic treatments, said appliance comprising:
    an elongated first component;

an elongated second component connected or connectable to said first elongated component to form an extension thereof in a longitudinal direction, whereby the elongated components cooperatively define a central body of the appliance spanning longitudinally between an anterior end of the first component and a distal end of the second component;

a first terminal head carried at the anterior end of the first component, said first terminal head comprising a first base pad facing laterally outward from the elongated first component and adapted for attachment to a first tooth of a dental arch; and a second terminal head carried at the distal end of the second component, said second terminal head comprising a second base pad facing laterally outward from the elongated second component in a same direction as the first base pad and adapted for attachment to a second tooth of said same dental arch; and a ratchet mechanism comprising a set of ratchet teeth defined on one of said first and second components, a ratchet pawl defined on the other of said first and second components and configured to engage with the ratchet teeth, and an operating lever configured for selective actuation to move the ratchet pawl into a release position disengaged from the ratchet teeth;

wherein said first and second components are arranged for selective longitudinal displacement relative to one another to adjust an overall length of the central body to adapt to a patient-specific mesial-distal distance between said first and second teeth of said dental arch; and the ratchet mechanism is arranged to lock said first and second components against said selective longitudinal displacement in a first direction when said ratchet pawl engages the ratchet teeth, allow said selective longitudinal displacement in an incremental fashion in a second direction when said ratchet pawl engages the ratchet teeth, and allow said selective longitudinal displacement in a free-sliding fashion in the first direction when the ratchet pawl is in the release position disengaged from the ratchet teeth; whereby said longitudinal displacement in said incremental fashion enables user-selection from any of a fixed number of pre-determined selectable lengths of said central body.

2. The distalization appliance of claim 1 wherein said first and second components are lockable to one another at any of a plurality of user-selectable lengths of said central body.

3. The distalization appliance of claim 2 wherein the first and second components are self-locking to one another at each of said user-selectable lengths.

4. The distalization appliance of claim 2 wherein the first and second components are adapted to have a greater locking strength against displacement in a collapsing direction reducing the overall length of the central body than in an extending direction increasing the overall length of the central body.

5. The distalization appliance of claim 1 wherein the first and second components are adapted for incremental displacement therebetween to enable user-selection from any of a fixed number of pre-determined selectable lengths of said central body.

6. The distalization appliance of claim 5 wherein the first and second components are adapted for said incremental displacement in a direction increasing the overall length of the central body.

7. The distalization appliance of claim 5 wherein the first and second components are adapted for incremental displacement in increments of less than 1-mm.

8. The distalization appliance of claim 1 wherein said one of the first and second components with the ratchet teeth is a male insertion component with an insertion end, and said other of the first and second components with the ratchet pawl is a female tubular component with a hollow interior in which the insertion end of said one of the first and second components with the ratchet teeth is received or receivable.

9. The distalization appliance of claim 8 wherein the female tubular component comprises an opening in a circumferential wall thereof by which the operating lever is accessible from outside the female tubular component.

10. The distalization appliance of claim 8 wherein the release lever is configured to be actuated by depression thereof inwardly into the hollow interior of the of the female tubular component, and to thereby move the ratchet pawl in an opposing direction out of engagement with the ratchet teeth.

11. The distalization appliance of claim 1 wherein said first and second components each have an arcuate curvature in the longitudinal direction, and the ratchet teeth and the ratchet pawl are defined on concave sides of the arcuate curvatures of the components.

12. The distalization appliance of claim 1 wherein at least one of the first and second terminal heads is connected to the respective one of the first and second components by a respective single axis rotational joint by which said one of the first and second terminal heads is rotatable relative to the respective one of the first and second components about a singular axis shared thereby at said joint.

13. The distalization appliance of claim 12 comprising two respective single-axis rotational joints by which the first and second terminal heads are rotatably connected to the first and second components, respectively, for rotation relative thereto about first and second axes.

14. The distalization appliance of claim 12 wherein the single-axis rotational joint comprises at least one threaded screw joint.

15. A method of using the distalization appliance of claim 1, said method comprising performing said relative longitudinal displacement of the first and second components to adjust the overall length of the central body according to the patient-specific mesial-distal distance between said first and second teeth of said dental arch, and attaching the first and second terminal heads to said first and second teeth of said dental arch with the central body set according to said patient-specific mesial-distal distance.

16. The method of claim 15 wherein performing said relative longitudinal displacement comprises lengthening said central body incrementally in the second direction via a ratcheting action between the ratchet teeth and the ratchet pawl, overshooting a targeted length during said lengthening, and collapsing said central body back toward said targeted length by actuating the operating lever to move the ratchet pawl to the release position disengaged from the ratchet teeth, and while holding the operating lever to maintain said release position of the ratchet pawl, then shortening the central body via free-sliding displacement between the first and second components in the first direction.

17. The distalization appliance of claim 1, wherein each of said first and second base pads is a mesh pad.

18. The distalization appliance of claim 1 wherein the elongated members both have an arcuate curvature in the longitudinal direction, and the first and second base pads face laterally outward from the elongated first and second components on a concave side of said arcuate curvature.

19. The distalization appliance of claim 1 wherein the release lever and the ratchet pawl are pivotable together about a shared pivot point, and reside on opposite sides of said pivot point.

20. The distalization appliance of claim 19 wherein said pivot point is defined by a pivot pin on which the release lever and the ratchet pawl are pivotable.

21. The distalization appliance of claim 1 wherein the release lever is configured to be actuated in a third direction toward the ratchet teeth, and to thereby move the ratchet pawl in an opposing fourth direction out of engagement with the ratchet teeth.

* * * * *